United States Patent [19]

Shida et al.

[11] Patent Number: 4,902,805
[45] Date of Patent: Feb. 20, 1990

[54] DERIVATIVES OF DIHYDROTRIAZOLE, AND HERBICIDAL COMPOSITIONS CONTAINING THE SAME AS AN ACTIVE INGREDIENT

[75] Inventors: Takafumi Shida; Takeo Watanabe; Shiro Yamazaki; Hiroyasu Shinkawa; Keigo Satake, all of Iwaki, Japan

[73] Assignee: Kureha Kagaku Kogyo Kabushiki Kaisha, Tokyo, Japan

[21] Appl. No.: 820,948

[22] Filed: Jan. 21, 1986

[30] Foreign Application Priority Data

Jan. 23, 1985 [JP] Japan .................................. 60-10623
Mar. 15, 1985 [JP] Japan .................................. 60-51700

[51] Int. Cl.$^4$ .................. A01N 43/653; C07D 249/10
[52] U.S. Cl. ..................................... 548/262; 549/473
[58] Field of Search ..................... 548/262, 265; 71/92

[56] References Cited

U.S. PATENT DOCUMENTS

| 4,049,812 | 9/1977 | Kuwada et al. | 514/220 |
| 4,492,597 | 1/1985 | Aoki et al. | 548/262 |
| 4,510,136 | 4/1985 | Moberg | 548/107 |

FOREIGN PATENT DOCUMENTS

| A0070089 | 1/1983 | European Pat. Off. | 548/262 |
| A2526271 | 11/1983 | France | 548/262 |
| 58-185572 | 10/1983 | Japan . | |

OTHER PUBLICATIONS

R. S. Tewari et al., *Tetrahedron*, vol. 39, No. 1, pp. 129–136, 1983.

Temple, Jr., Heterocyclic Components "Triazoles 1,2,4", N.Y.: John Wiley & Sons, p. 64 (1981).
P. K. Kadaba, Journal of Pharmaceutical Sciences, vol. 59, No. 8, Aug. 1970, pp. 1190–1191.

*Primary Examiner*—Richard L. Raymond
*Assistant Examiner*—Patricia L. Morris
*Attorney, Agent, or Firm*—John P. White

[57] ABSTRACT

Disclosed herein are a derivative of dihydrotriazole represented by the general formula (I):

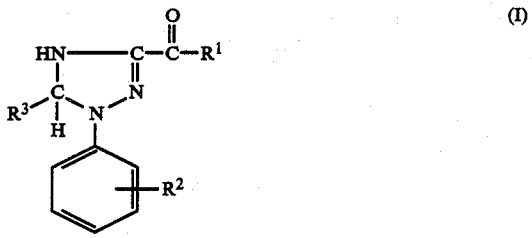

wherein $R^1$ represents an amino group, lower alkoxy group, or lower alkyl amino group, $R^2$ represents a hydrogen atom, halogen atom, or lower alkyl group and $R^3$ represents a hydrogen atom, lower alkyl group, benzyl group, furyl group, phenyl group or phenyl group substituted with a halogen atom, hydroxyl group, carboxyl group, methoxycarbonyl group, lower alkyl group or lower alkoxy group, and a herbicidal composition containing as an active ingredient at least one of the derivatives of dihydrotriazole.

7 Claims, No Drawings

DERIVATIVES OF DIHYDROTRIAZOLE, AND HERBICIDAL COMPOSITIONS CONTAINING THE SAME AS AN ACTIVE INGREDIENT

DETAILED EXPLANATION OF THE INVENTION

The present invention relates to a novel derivative of dihydrotriazole represented by the formula (I):

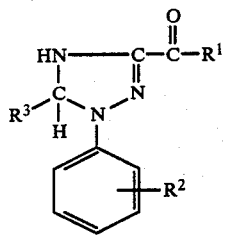

(I)

wherein $R^1$ represents an amino group, lower alkoxy group, or lower alkyl amino group, $R^2$ represents a hydrogen atom, halogen atom, or lower alkyl group, and $R^3$ represents a hydrogen atom, lower alkyl group, benzyl group, furyl group, phenyl group or phenyl group substituted with a halogen atom, hydroxyl group, carboxyl group, methoxycarbonyl group, lower alkyl group, or lower alkoxy group, and a herbicidal composition containing as the active ingredient at least one of the derivatives of dihydrotriazole.

Rice, wheat and corn are the important crops and it is indispensable to protect these crops from weeds' harm by the use of herbicide. Recently, a selective herbicide which kills weeds only and does not severely injure crops even when the herbicide is applied to the field where a crop and a weed grow together, is strongly desired.

The inventors of the present invention studied for finding a compound which satisfy this requirement and have found a derivative of dihydrotriazole represented by the formula (I) having an excellent selective herbicidal effect, and the present invention has been attained based on the findings.

In a first aspect of the present invention, there is provided a derivative of 4,5-dihydro-1,5-disubstituted-1H-1,2,4-triazole-3-carboxylic acid represented by the formula (I):

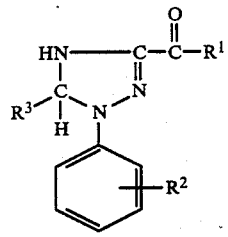

(I)

wherein $R^1$ represents an amino group, lower alkoxy group, or lower alkyl amino group, $R^2$ represents a hydrogen atom, halogen atom, or lower alkyl group, and $R^3$ represents a hydrogen atom, lower alkyl group, benzyl group, furyl group, phenyl group or phenyl group substituted with a halogen atom, hydroxyl group, carboxyl group, methoxycarbonyl group, lower alkyl group, or lower alkoxy group.

In a second aspect of the present invention, there is provided a process for producing a derivative of 4,5-dihydro-1,5-disubstituted-1H-1,2,4-triazole-3-carboxylic acid represented by the formula (I), which comprises reacting a derivative of amino(phenylhydrazono)acetic acid of the following formula (II):

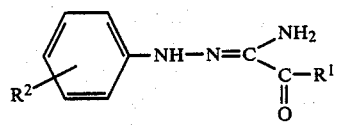

(II)

wherein $R^1$ represents an amino group, lower alkoxy group, or lower alkyl amino group and $R^2$ represents a hydrogen atom, halogen atom, or lower alkyl group, with aldehyde of following formula (III):

$R^3$—CHO  (III)

wherein $R^3$ represents a hydrogen atom, lower alkyl group, benzyl group, furyl group, phenyl group or phenyl group substituted with a halogen atom, hydroxyl group, carboxyl group, methoxycarbonyl group, lower alkyl group or lower alkoxy group, under the existence of acid catalyst.

In a third aspect of the present invention, there is provided a herbicidal composition comprising as the active ingredient a herbicidally effective amount of at least one derivative of 4,5-dihydro-1,5-disubstituted-1H-1,2,4-triazole-3-carboxylic acid of the following formula (I):

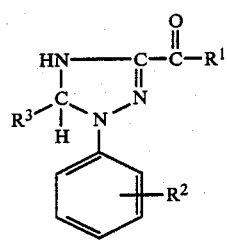

(I)

wherein $R^1$ represents an amino group or lower alkyl amino group, $R^2$ represents a hydrogen atom, halogen atom, or lower alkyl group, and $R^3$ represents a hydrogen atom, lower alkyl group, benzyl group, furyl group, phenyl group or phenyl group substituted with a halogen atom, hydroxyl group, carboxyl group, methoxycarbonyl group, lower alkyl group, or lower alkoxy group, and a diluent therefor.

In a fourth aspect of the present invention, there is provided a method for killing weeds which comprises applying to weeds or the locus thereof a herbicidally effective amount of at least one derivative of 4,5-dihydro-1,5-disubstituted-1H-1,2,4-triazole-3-carboxylic acid of the following formula (I):

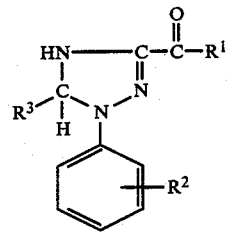

(I)

wherein R¹ represents an amino group or lower alkyl amino group, R² represents a hydrogen atom, halogen atom, or lower alkyl group, and R³ represents a hydrogen atom, lower alkyl group, benzyl group, furyl group, phenyl group or phenyl group substituted with a halogen atom, hydroxyl group, carboxyl group, methoxycarbonyl group, lower alkyl group, or lower alkoxy group.

The compounds of the present invention represented by the formula (I) (hereinafter referred to as "the present compound") are novel compounds, and show a herbicidal activity against weeds of true grasses (Gramineae) and broad-leaved weeds, especially excellent herbicidal activity against broadleaved weeds according to the herbicidal tests in folier application and soil treatment. Besides, since it does not show any severe injury to important crops such as rice, wheat and corn, it can broadly applied to rice pads and fields. Since it has a proper transport property to soil, it can also be applied to orchards and flower plantations.

The present compounds having a herbicidal activity, represented by the formula (I) are easily synthesized as follows.

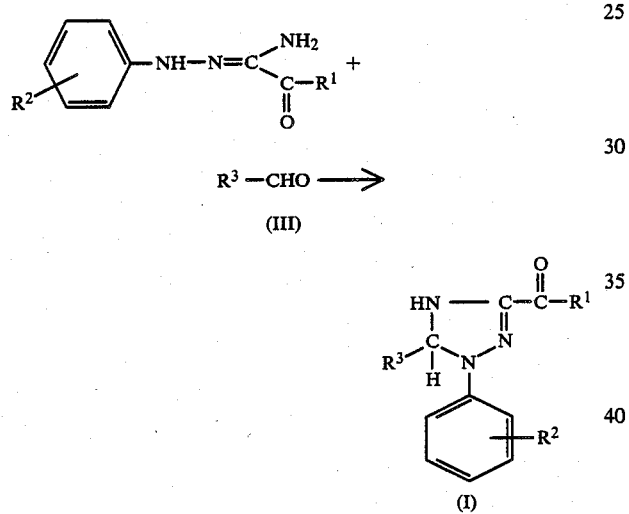

wherein each of R¹, R² and R³ are defined as above.

Namely, a derivative of amino(phenylhydrazono)-acetic acid (II) is reacted with aldehyde (III) by dehydration at a temperature of −20°-300° C., preferably 0°-200° C. in the presence of acid catalyst in an inert solvent. In the reaction, it is necessary to take place no dehydrogenation of the produced derivative of dihydrotriazole. If a derivative of dihydrotriazole is dehydrated, unnecessary derivative of triazole will be produced and the yield of dihydrotriazole is lowered. To prevent such unnecessary side reaction and have a better yield of dihydrotriazole, it is necessary to deoxidize the solvent in advance and further proceed the reaction under an inert atmosphere. However, in case a derivative of dihydrotriazole is insoluble in the reaction solvent and almost all the derivative produced crystallize during the reaction, the reaction can be carried out under an inert atmosphere.

As an acid catalyst, organic acid such as p-toluene sulphonic acid and benzene sulphonic acid, or inorganic acid such as sulphuric acid and phosphoric acid is used. However, in case an acidic solvent which has acid catalytic acitivity such as formic acid, acetic acid, propionic acid, the mixture thereof, or one of these solvents diluted with small amount of water or other solvent is used, it is unnecessary to use such acid catalyst.

As a solvent, any solvent which does not react with amines represented by the formula (II) and aldehydes represented by the formula (III) can be used. For example, an aromatic solvent such as benzene, toluene, xylene, monochlorobenzene and dichlorobenzene, an ester-type solvent such as ethyl acetate, a chlorinated solvent such as carbon tetrachloride, chloroform and dichloroethane, or an acidic solvent mentioned above can be used.

When an azeotropic distillation is taken place during the reaction to proceed such dehydration effectively, a solvent which does not mix with water should be selected. When an acidic solvent mentioned above is used, the reaction can go at room temperature.

The present compounds prepared by above reaction are concretely shown in Table 1 with their respective melting point.

TABLE 1

| Number of present compound | Atom or Group | | | Melting point (°C.) |
|---|---|---|---|---|
| | R¹ | R² | R³ | |
| 1 | NH₂ | H | phenyl | 208–211 |
| 2 | NH₂ | H | 4-CH₃-phenyl | 194–197 |
| 3 | NH₂ | H | 4-Cl-phenyl | 213–215 |
| 4 | NH₂ | H | 2-HO-phenyl | 182–184 |
| 5 | NH₂ | H | 3-OH-phenyl | 174–176 |
| 6 | NH₂ | H | 4-OH-phenyl | 210–213 |
| 7 | NH₂ | H | 2-HOOC-phenyl | 145–147 |
| 8 | NH₂ | 3-CH₃ | phenyl | 193–195 |

TABLE 1-continued

| Number of present compound | Atom or Group R¹ | R² | R³ | Melting point (°C.) |
|---|---|---|---|---|
| 9 | NH₂ | 3-CH₃ | 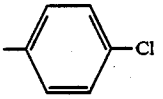 | 195-198 |
| 10 | NH₂ | 3-CH₃ | 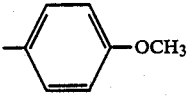 | 176-179 |
| 11 | NH₂ | 3-CH₃ | 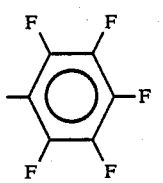 | ca. 140 (decomposed) |
| 12 | NH₂ | 4-Cl | 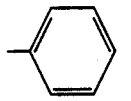 | 199-201 |
| 13 | NH₂ | 4-Cl | 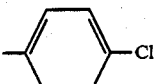 | 121-122 |
| 14 | NH₂ | 4-Cl | 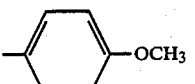 | 176-178 |
| 15 | NH₂ | H | 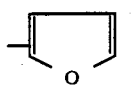 | 183-186 |
| 16 | OCH₃ | H | 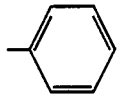 | 148-149 |
| 17 | OCH₃ | H | 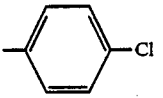 | 143-145 |

The present invention will be more precisely explained while referring to the following Examples. However, the present invention is not restricted to Examples under mentioned. From the foregoing description, one skilled in the art can easily ascertain the essential characteristics of this invention, and without departing from the spirit and scope thereof, can make various changes and modifications of the invention to adapt it to various usages and conditions.

EXAMPLE 1

Synthesis of 5-(4-chlorophenyl)-4,5-dihydro-1-phenyl-1H-1,2,4-triazole-3-carboxamide (compound No. 3)

Into 50 ml of benzene, 1.8 g of starting material, compond (II) (R¹=NH₂, R²=H), and 2.1 g of p-chlorobenzaldehyde were added together with 20 mg of p-toluene sulphonic acid as an acid catalyst, and refluxed 10 hours with an apparatus thereby separating water as the benzene azeotrope. After cooling, the product was separated by filtration and obtained 3.0 g of compound No. 3 (94% yield). The physical properties of the compound are;

Melting point; 213°-215° C.

Infrared spectrum, (KBr, cm⁻¹); $\nu$NH 3380, 3260, 3200; $\nu$CO 1660.

NMR spectrum (d₆-DMSO) δ (ppm); 6.40 (1H, S: CH<); 6.6-8.1 (12H, m; ArH+NH+NH₂).

EXAMPLE 2

Synthesis of 4,5-dihydro-1-(3-methylphenyl)-5-phenyl-1H-1,2,4-triazole-3-carboxamide (compound No. 8)

Into 50 ml of deoxidized benzene, 3.0 g of starting material, compound (II) (R¹=NH₂, R²=3-CH₃), and 2.1 g of benzaladehyde were added together with 25 mg of p-toluene sulphonic acid as an acid catalyst and refluxed 3 hours under nitrogen atmosphere with the same apparatus as EXAMPLE 1. After cooling, the product was separated by filtration and obtained 4.1 g of crystal, compound No. 8 (94% yield). The physical properties of the compound are set forth below.

Melting point; 193°-195° C.

Infrared spectrum (KBr, cm⁻¹); $\nu$NH 3380, 3290, 3170; $\nu$CO 1660.

NMR spectrum (d₆-DMSO) δ (ppm); 2.23 (3H, S; CH₃); 6.50 (1H, S; CH<); 6.6-8.4 (13 H, m; ArH+NH+NH₂).

Mass spectrum (m/z, relative intensity); 280 (M⁺, 55%) 279 (20%), 278 (15%), 262 (14%), 203 (100%), 186 (78%).

EXAMPLE 3

Synthesis of 4,5-dihydro-1-(3-methylphenyl)-5-phenyl-1H-1,2,4-triazole-3-carboxamide (compound No. 8)

Into 150 ml of deoxidized acetic acid, 19.2 g of starting material, compound (II) (R¹=NH₂, R²=3-CH₃), and 11.7 g of benzaldehyde were added and stirred 1.5 hours at room temperature under nitrogen atmosphere. Crystalline product was separated by filtration, washed with 20 ml of deoxidized acetic acid. The thus washed product is dried in a KOH desiccator and 22.5 g of compound No. 8 (80.5% yield) was obtained.

PREPARATION EXAMPLE 1

By mixing 50 parts by weight of compound No. 1, 5 parts by weight of lignin sulfonate, 3 parts by weight of alkyl sulphonate and 42 parts by weight of diatomite and pulverizing the mixture, a wettable powder was prepared.

The thus prepared wettable powder is applied after diluting with water to a suitable concentration of compound No. 1 as the active ingredient.

PREPARATION EXAMPLE 2

After uniformly mixing 8 parts by weight of compound No. 6, 40 parts by weight of bentonite, 45 parts by weight of clay and 7 parts by weight of lignin sulphonate, the mixture was kneaded with water and processed into granules by an extruding granulator and dried.

The effectiveness of the present compound is explained while referring to the following herbicidal examples.

HERBICIDAL TEST EXAMPLE 1

Pre-emergence herbicidal effect against field weeds

After certain amounts of seeds of the following plants were sown on a soil packed in a planter of a size of 650×210×200 mm and covered with a thin layer of soil respectively, a dilute solution of the present compound (concentration had been adjusted to correspond to 50 g/are) was uniformly sprayed on the surface of the soil. The planter, then, was kept under a growth management in a green house.

Name of the plants tested

Weeds:
  Echinochloa crus-galli
  Cyperus iria
  Poa annua
  Stallaria media
  Cardamine flexuosa
  Bidens frondosa
  Portulaca oleracea
  Euxolus ascendens
  Persicaria logiseta Crops:
  Corn
  Soy-bean plant
  Cotton plant
  Wheat After 25 days of the treatment, the state of the plants was observed to assess the damage due to the application of the solution to evaluate the herbicidal activity against the weeds and damage to the crops according to the following criteria.

| Criteria of Evaluation | |
|---|---|
| Herbicidal activity | Damage |
| 0 No effect | − None |
| 1 20% effective | ± Minute |
| 2 40% effective | + Slight |
| 3 60% effective | ++ Medium |
| 4 80% effective | +++ Severe |
| 5 100% effective | ++++ Dead |

HERBICIDAL TEST EXAMPLE 2

Post-emergence herbicidal effect against field weeds

Certain amounts of seeds of the same plants as TEST EXAMPLE 1 were sown on a soil packed in a planter of a size of 650×210×200 mm, covered with a thin layer of soil respectively, and kept under a growth management in a green house. At the time the crops and weeds reached to a two to three leaf stage, an aqueous suspension of the present compound (concentration had been adjusted to correspond to 50 g/are) was uniformly sprayed on the surface of the foliage and the soil. Then, the planter was kept under a growth management in a green house again. After two to five days of the treatment, the state was observed and evaluated according to the same criteria as TEST EXAMPLE 1 and the results are shown in Table 3.

HERBICIDAL TEST EXAMPLE 3

Herbicidal effect against rice-pad weeds by soil treatment before rice plantation Three pots, each of plantable area is 1/5000 are, are packed with soil and adjusted to a rice-pad like state. One pot was sown with Echinochloa crus-galli in two steps so that one group of the weed was three-leaf stage and another group was before germination at the time of treatment. Second pot was sown with Cyperus microiria in two steps so that one group of the weed was two-leaf stage and another group was before germination at the time of treatment. Third pot had no weed seeds.

Each of the pot was treated with the aqueous suspension of the present compound putting it into water layer of the pot in an amount corresponding to 30 g/are of active ingredient. After 3 days of the treatment, the third pot was planted with seedlings of rice plant. All the pots were kept under growth management in a green house. After 25 days of the treatment, the state was observed and evaluated according to the same criteria as TEST EXAMPLE 1 and the results are shown in Table 4.

TABLE 2

| Plant | Number of present compound | | | | | | | | | | | | Not treated |
|---|---|---|---|---|---|---|---|---|---|---|---|---|---|
| | 1 | 2 | 3 | 4 | 5 | 6 | 8 | 9 | 10 | 12 | 13 | 14 | |
| Weeds | Herbicidal activity against weeds | | | | | | | | | | | | |
| Echinochloa crus-galli | 4 | 5 | 4 | 5 | 5 | 5 | 5 | 5 | 5 | 4 | 4 | 4 | 0 |
| Cyperus iria | 5 | 5 | 4 | 5 | 5 | 5 | 5 | 5 | 5 | 5 | 4 | 4 | 0 |
| Poa annua | 5 | 5 | 4 | 4 | 4 | 4 | 4 | 5 | 5 | 4 | 5 | 5 | 0 |
| Stallaria media | 5 | 5 | 5 | 5 | 5 | 5 | 5 | 5 | 5 | 5 | 4 | 4 | 0 |
| Cardamine flexuosa | 5 | 5 | 5 | 5 | 5 | 5 | 5 | 5 | 5 | 5 | 5 | 5 | 0 |
| Bidens frondosa | 5 | 5 | 4 | 5 | 5 | 5 | 5 | 5 | 5 | 5 | 5 | 5 | 0 |
| Portulaca oleracea | 5 | 5 | 4 | 4 | 4 | 5 | 5 | 5 | 5 | 5 | 5 | 4 | 0 |
| Euxolus ascendens | 5 | 5 | 5 | 5 | 5 | 5 | 5 | 5 | 5 | 5 | 5 | 5 | 0 |
| Persicaria logiseta | 5 | 5 | 5 | 5 | 5 | 5 | 5 | 5 | 5 | 4 | 5 | 5 | 0 |
| Crops | Damage to crops | | | | | | | | | | | | |
| Corn | − | − | − | − | − | − | − | − | − | − | − | − | − |
| Soy-bean plant | + | − | − | − | − | − | − | + | + | − | − | − | − |
| Cotton plant | − | − | − | − | − | − | − | − | − | − | − | − | − |
| Wheat | − | − | − | − | − | − | − | − | − | − | − | − | − |

TABLE 3

| Plant | 1 | 2 | 3 | 4 | 5 | 6 | 8 | 9 | 10 | 12 | 13 | 14 | Not treated |
|---|---|---|---|---|---|---|---|---|---|---|---|---|---|
| Weeds | Herbicidal activity against weeds | | | | | | | | | | | | |
| Echinochloa crus-galli | 3 | 5 | 3 | 4 | 5 | 5 | 5 | 4 | 4 | 3 | 4 | 3 | 0 |
| Cyperus iria | 4 | 5 | 4 | 5 | 5 | 5 | 4 | 4 | 5 | 4 | 3 | 3 | 0 |
| Poa annua | 4 | 4 | 4 | 5 | 4 | 3 | 5 | 4 | 4 | 5 | 4 | 0 | |
| Stallaria media | 5 | 5 | 5 | 5 | 5 | 5 | 5 | 5 | 5 | 5 | 5 | 5 | 0 |
| Cardamine flexuosa | 5 | 5 | 5 | 5 | 5 | 5 | 5 | 5 | 5 | 5 | 5 | 5 | 0 |
| Bidens frondosa | 5 | 5 | 5 | 5 | 5 | 5 | 5 | 5 | 5 | 5 | 5 | 5 | 0 |
| Portulaca oleracea | 5 | 5 | 5 | 4 | 5 | 4 | 5 | 5 | 5 | 4 | 5 | 4 | 0 |
| Euxolus ascendens | 5 | 5 | 5 | 5 | 5 | 5 | 5 | 5 | 5 | 5 | 5 | 5 | 0 |
| Persicaria logiseta | 5 | 5 | 5 | 5 | 5 | 5 | 5 | 5 | 4 | 4 | 5 | 4 | 0 |
| Crops | Damage to crops | | | | | | | | | | | | |
| Corn | − | − | − | − | − | − | − | − | − | − | − | − | − |
| Soy-bean plant | + | − | − | − | + | − | − | + | + | + | + | − | − |
| Cotton plant | − | − | − | − | − | − | − | − | − | − | − | − | − |
| Wheat | − | − | − | − | − | − | − | − | − | − | − | − | − |

TABLE 4

| Plant | 1 | 2 | 3 | 4 | 5 | 6 | 8 | 9 | 10 | 12 | 13 | 14 | Not treated |
|---|---|---|---|---|---|---|---|---|---|---|---|---|---|
| Weeds | Herbicidal activity against weeds | | | | | | | | | | | | |
| Echinochloa crus-galli | | | | | | | | | | | | | |
| 3 leaf stage | 4 | 5 | 4 | 5 | 5 | 5 | 5 | 5 | 4 | 4 | 3 | 4 | 0 |
| pre-germination | 5 | 5 | 5 | 5 | 5 | 5 | 5 | 5 | 5 | 5 | 5 | 5 | 0 |
| Cyperus microiria | | | | | | | | | | | | | |
| 2 leaf stage | 4 | 5 | 3 | 5 | 4 | 4 | 5 | 4 | 5 | 4 | 4 | 4 | 0 |
| pre-germination | 5 | 5 | 4 | 5 | 5 | 5 | 5 | 5 | 5 | 5 | 4 | 5 | 0 |
| Crops | Damage to crops | | | | | | | | | | | | |
| rice plant | − | − | − | − | − | − | − | − | − | − | − | − | − |

What is claimed is:

1. A derivative of 4,5-dihydro-1,5-disubstituted-;b 1H-1,2,4-triazole-3-carboxylic acid represented by the formula (I):

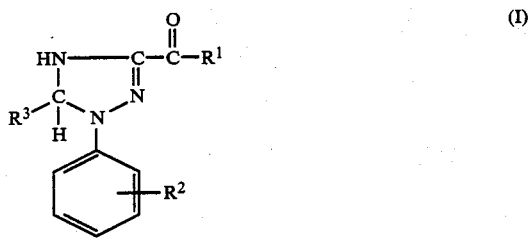

wherein $R^1$ represents an amino group, or lower alkyl amino group, $R^2$ represents a hydrogen atom, halogen atom, or lower alkyl group, and $R^3$ represents a hydrogen atom, lower alkyl group, benzyl group, furyl group, phenyl group or phenyl group substituted with a halogen atom, hydroxyl group, carboxyl group, methoxycarbonyl group, lower alkyl group, or lower alkoxy group.

2. A derivative according to claim 1, wherein $R^1$ represents an amino group, $R^2$ represents a hydrogen atom, halogen atom, or lower alkyl group, and $R^3$ represents a phenyl group, or phenyl group substituted with a halogen atom, hydroxy group, lower alkyl group, or lower alkoxy group.

3. A derivative according to claim 1, wherein $R^1$ represents an amino group, $R^2$ represents a hydrogen atom, and $R^3$ represents a phenyl group, 3-methylphenyl group, 4-chlorophenyl group, 2-hydroxyphenyl group, 3-hydroxyphenyl group, 4-hydroxyphenyl group, 2-carboxyphenyl group, or furyl group.

4. A derivative according to claim 1, wherein $R^1$ represents an amino group, $R^2$ represents 3-methyl group, and $R^3$ represents a phenyl group, 4-chlorophenyl group, 4-methoxyphenyl group, or 2,3,4,5,6-pentafluorophenyl group.

5. A derivative according to claim 1, wherein $R^1$ represents an amino group, $R^2$ represents 4-chlorine atom, and $R^3$ represents a phenyl group, 4-chlorophenyl group, or 4-methoxyphenyl group.

6. A derivative according to claim 1, wherein $R^1$ represents an amino group, $R^2$ represents a hydrogen atom, and $R^3$ represents 4-chlorophenyl group.

7. A derivative according to claim 1, wherein $R^1$ represents an amino group, $R^2$ represents 3-methyl group, and $R^3$ represents a phenyl group.

* * * * *